(12) United States Patent
Hu

(10) Patent No.: US 10,154,802 B2
(45) Date of Patent: Dec. 18, 2018

(54) METHOD AND APPARATUS FOR PRECISELY PERCEIVING INDOOR ACTIVITY

(71) Applicant: Shenzhen Zhiying Technologies Co., Ltd., Shenzhen, Guangdong OT (CN)

(72) Inventor: Kun Hu, Guangdong (CN)

(73) Assignee: Shenzhen Zhiying Technologies Co., Ltd., Shenzhen (CN)

( * ) Notice: Subject to any disclaimer, the term of this patent is extended or adjusted under 35 U.S.C. 154(b) by 334 days.

(21) Appl. No.: 15/095,219

(22) Filed: Apr. 11, 2016

(65) Prior Publication Data

US 2016/0278668 A1 Sep. 29, 2016

Related U.S. Application Data

(63) Continuation of application No. PCT/CN2014/088143, filed on Oct. 8, 2014.

(30) Foreign Application Priority Data

Oct. 10, 2013 (CN) .......................... 2013 1 0478595

(51) Int. Cl.
*G01V 1/00* (2006.01)
*A61B 5/11* (2006.01)
*A61B 5/00* (2006.01)

(52) U.S. Cl.
CPC ........... *A61B 5/1118* (2013.01); *A61B 5/1123* (2013.01); *A61B 5/1126* (2013.01); *A61B 5/6889* (2013.01); *G01V 1/001* (2013.01); *A61B 5/1113* (2013.01); *A61B 2505/07* (2013.01); *A61B 2562/0204* (2013.01)

(58) Field of Classification Search
CPC ... A61B 5/1118; A61B 5/6889; A61B 5/1126; A61B 5/1123; A61B 2505/07; A61B 5/1113; A61B 2562/0204; G01V 1/001
See application file for complete search history.

(56) References Cited

U.S. PATENT DOCUMENTS

| | | | | |
|---|---|---|---|---|
| 4,001,771 A | * | 1/1977 | Amrine | G01S 11/14 340/517 |
| 4,558,439 A | * | 12/1985 | Gu/ desen | G01S 3/8036 367/127 |
| 9,435,873 B2 | * | 9/2016 | Regunathan | G01S 3/8006 |

(Continued)

FOREIGN PATENT DOCUMENTS

CN     1808171 A     7/2006

OTHER PUBLICATIONS

International Search Report of PCT Patent Application No. PCT/CN2014/088143 dated Dec. 15, 2014.

*Primary Examiner* — Hovhannes Baghdasaryan

(57) ABSTRACT

The present invention discloses a method and an apparatus for precisely perceiving an indoor activity. The method may include: receiving a vibration signal on a floor by using multiple vibration sensors disposed according to a preset rule; and determining a location of a vibration source according to a phase difference of a vibration signal of the same vibration source in different vibration sensors. The monitoring performed on the indoor activity in the present invention can be performed without disturbing the monitored person, and can resolve the concern about leakage of privacy of the monitored person.

6 Claims, 3 Drawing Sheets

(56) References Cited

U.S. PATENT DOCUMENTS

| | | | |
|---|---|---|---|
| 2001/0033246 A1* | 10/2001 | Burchett | G01S 3/7864 |
| | | | 342/91 |
| 2007/0219742 A1* | 9/2007 | Workman | G01N 29/0618 |
| | | | 702/150 |
| 2015/0168538 A1* | 6/2015 | Bradley | G01S 5/0257 |
| | | | 367/127 |

* cited by examiner

METHOD AND APPARATUS FOR PRECISELY PERCEIVING INDOOR ACTIVITY

CROSS-REFERENCE TO RELATED APPLICATIONS

The present application is a Continuation Application of PCT application No. PCT/CN2014/088143 filed on Oct. 8, 2014, which claims the benefit of Chinese Patent Application No. 201310478595.7 filed on Oct. 10, 2013, the contents of which are hereby incorporated by reference.

TECHNICAL FIELD

The present invention relates to the technical field of vibration perception, and in particular, to a method and an apparatus for precisely perceiving an indoor activity.

BACKGROUND

In the prior art, in order to learn about indoor activity information (generally of a person), a human body generally needs to wear a sensing device, or a video monitoring device is generally used.

The sensing device is normally usable only when the sensing device is worn on the human body, which is relatively troublesome; and the monitoring device tends to cause leakage of personal privacy in daily life, and is complicated in recognizing and calculating, and is currently unsuitable for commercial application.

SUMMARY

A main objective of the present invention is to provide a method for precisely perceiving an indoor activity, which can perform effective monitoring on the indoor activity and is convenient and practical.

The present invention provides a method for precisely perceiving an indoor activity, including:

receiving a vibration signal on a floor by using multiple vibration sensors disposed according to a preset rule; and determining a location of a vibration source according to a phase difference of a vibration signal of the same vibration source in different vibration sensors.

Preferably, the step of determining a location of a vibration source according to a phase difference of a vibration signal of the same vibration source in different vibration sensors specifically includes:

acquiring an accurate location of the vibration source by performing phase shift analysis and sound speed calibration processing on the vibration signal in each vibration sensor and by performing calculation with a trigonometric function according to a fixed distance between the vibration sensors, where at least 3 vibration sensors are disposed, and a fixed distance is set between the vibration sensors.

Preferably, the vibration source is an indoor monitored human body, and the vibration signal is a pace signal of a monitored person, and the pace signal includes an impact, a stride, a cadence, and/or bilateral symmetry.

Preferably, the method further includes:

analyzing living habits of the monitored person according to a location and the pace signal of the monitored person and time.

Preferably, the method further includes:

performing statistics of pace signals of the monitored person in a time period, analyzing a change of the pace signals, and acquiring body condition change information of the monitored person; and/or performing statistics of building vibration spectrum information, and analyzing building change information according to a change of the vibration spectrum information.

The present invention further provides an apparatus for precisely perceiving an indoor activity, including:

a vibration perceiving module, configured to receive a vibration signal on a floor by using multiple vibration sensors disposed according to a preset rule; and a location analyzing module, configured to determine a location of a vibration source according to a phase difference of a vibration signal of the same vibration source in different vibration sensors.

Preferably, the location analyzing module is specifically configured to:

acquiring an accurate location of the vibration source by performing phase shift analysis and sound speed calibration processing on the vibration signal in each vibration sensor and by performing calculation with a trigonometric function according to a fixed distance between the vibration sensors, where at least 3 vibration sensors are disposed, and a fixed distance is set between the vibration sensors.

Preferably, the vibration source is an indoor monitored human body, and the vibration signal is a pace signal of a monitored person, and the pace signal includes an impact, a stride, a cadence, and/or bilateral symmetry.

Preferably, the device further includes:

a habit analyzing module, configured to analyze living habits of the monitored person according to a location and the pace signal of the monitored person and time.

Preferably, the device further includes:

a statistics and analyzing module, configured to: perform statistics of pace signals of the monitored person in a time period, analyze a change of the pace signals, and acquire body condition change information of the monitored person; and/or perform statistics of building vibration spectrum information, and analyze building change information according to a change of the vibration spectrum information.

The present invention may use the pace signal (impact strength, stride, cadence and/or bilateral symmetry and the like) of the monitored person to reflect the mental and health conditions of a person; use the change of the vibration, which is caused by the pace on the floor, to reflect long-term slow changes of the building; and keep a relatively detailed record of the daily life and the daily habits of the monitored person by recording and observing the daily indoor activity location. All the foregoing tasks are performed without disturbing the monitored person, and can resolve the concern about leakage of privacy of the monitored person, for example, the face, figure, and behavior of the monitored person.

The objective fulfillment, functional characteristics, and advantages of the present invention are hereinafter further described with reference to embodiments and accompanying drawings.

DESCRIPTION OF EMBODIMENTS

It should be understood that the specific embodiments described herein are merely used to explain the present invention but are not intended to limit the present invention.

Figure 1:
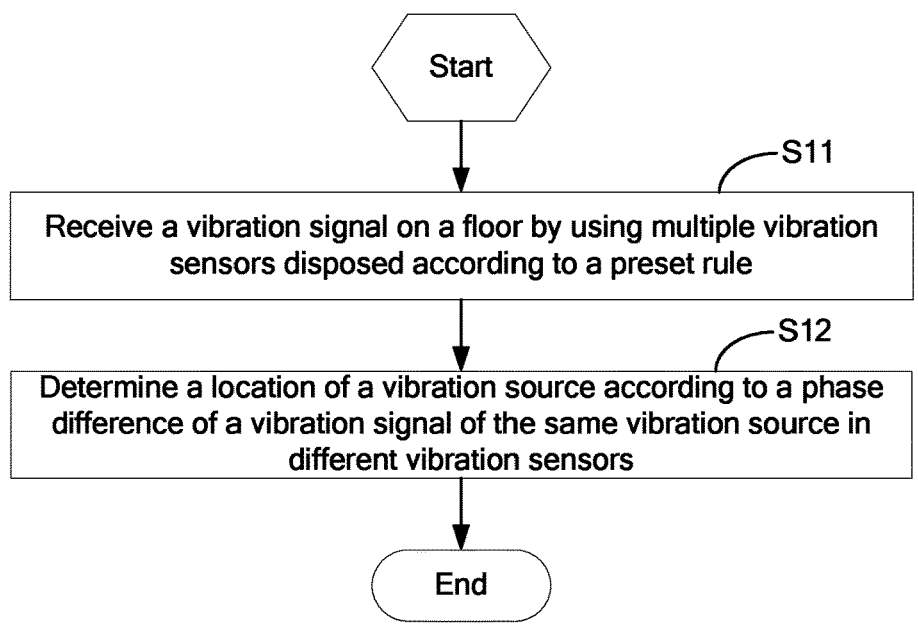
FIG. 1 is a schematic flowchart of steps in an embodiment of a method for precisely perceiving an indoor activity according to the present invention.

Referring to FIG. 1, an embodiment of a method for precisely perceiving an indoor activity according to the present invention is provided. The method may include:

Step S11: Receive a vibration signal on a floor by using multiple vibration sensors disposed according to a preset rule.

Step S12: Determine a location of a vibration source according to a phase difference of a vibration signal of the same vibration source in different vibration sensors.

According to the method for precisely perceiving the indoor activity, multiple vibration sensor that are at a relatively fixed distance between each other may sense the vibration caused by activities such as a walk on the floor, phase analysis may be performed on the vibration signals on the vibration sensors in different locations, the indoor movement of the vibration source (such as the monitored person) may be precisely located, and the information such as the activity status and the living habits of the monitored person is perceived.

The vibration source may be an indoor monitored human body, and the vibration signal may be a pace signal of the monitored person, and the pace signal may include an impact, a stride, a cadence, and/or bilateral symmetry or the like.

The vibration sensors disposed closely on the floor may sensitively perceive a slight vibration caused by the walk of a human being, the pass of an indoor truck, the fall of an object onto the ground, the locking of a door, and the like. The sensing of paces may be implemented by mathematical modeling. Although shoes and mental conditions impose a great influence on the impact caused by the walk, the stability of factors such as a basic house structure and a human weight makes the walk generate obviously distinguishable characteristics.

In this embodiment, there may be at least 3 vibration sensors, and a fixed distance is set between the vibration sensors; by performing phase shift analysis and sound speed calibration processing on the vibration signal in each vibration sensor, a scan similar to B-ultrasound may be performed; and the accurate location of the vibration source is acquired by performing calculation with a trigonometric function according to the fixed distance between the vibration sensors. In a specific embodiment of the present invention, for example, signals received by 5 sensors that are arranged in a row and at a fixed distance between each other may be fit at different delays, scan and interception may be performed in a sector area that is almost 180° wide. Each distinguishing unit in a scan surface has a special and fixed delay characteristic for a different sensor. Therefore, by fitting the signals of different delays, the vibration scenario of the scan surface can be completely displayed. The distinguishing unit in which the vibration source is located takes on a high signal amplitude, and other units are silent. Like the reception in the phased array B-ultrasound scan, the present invention can clearly reflect the return wave conditions of the scanned vector surface in an image form, and therefore, can acquire the accurate location of the vibration source.

Figure 2:
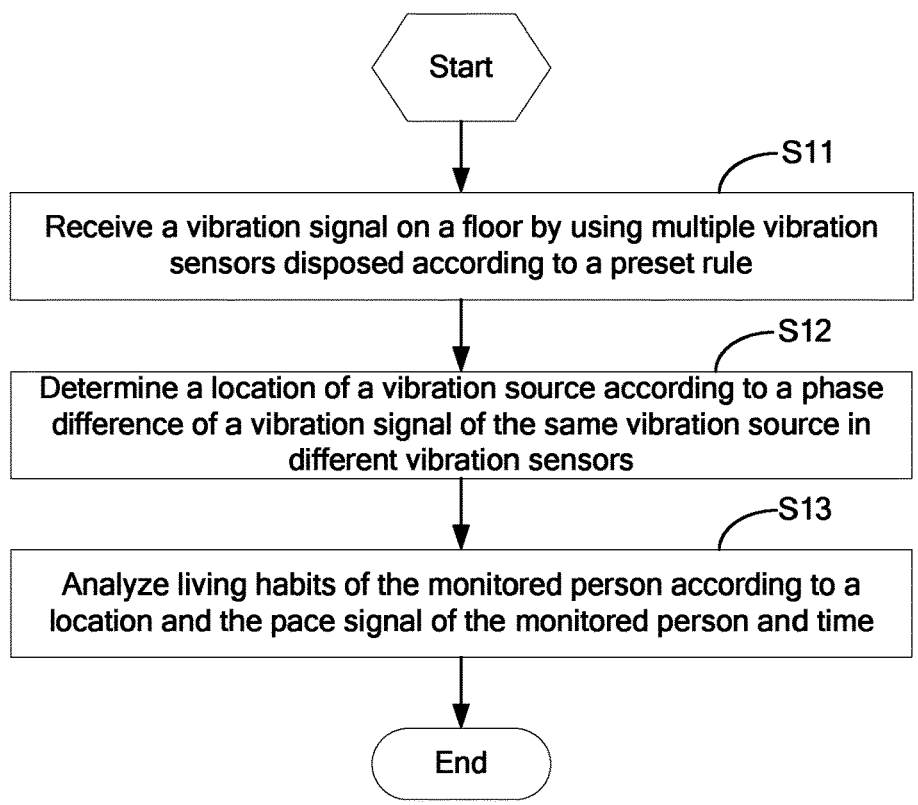
FIG. 2 is a schematic flowchart of steps in another embodiment of a method for precisely perceiving an indoor activity according to the present invention.

Referring to FIG. 2, in another embodiment of the present invention, after step S12, the method may further include:

Step S13: Analyze living habits of the monitored person according to a location and the pace signal of the monitored person and time.

The multiple vibration sensors that are at a relatively fixed distance between each other are disposed closely on the floor, and may perceive the vibration on the floor and acquire the location of the vibration source. In recognizing the pace signal of the monitored person, tracking may be started. By analyzing the phase difference of the pace signal on different sensors, the current location of the monitored person who is walking can be precisely determined. The daily habit, the living status and the like of the monitored object can be acquired by means of combined analysis on the location information, the pace signal, and the time background.

Figure 3:
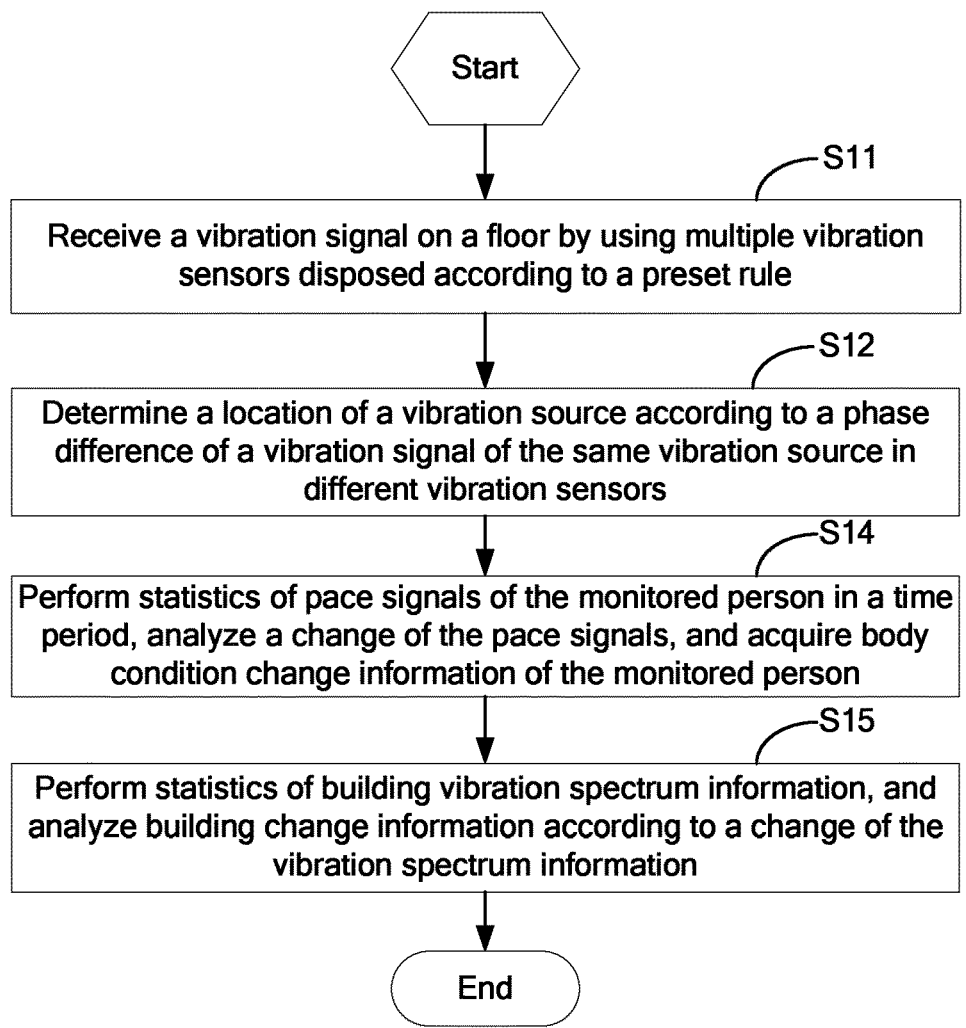
FIG. 3 is a schematic flowchart of steps in still another embodiment of a method for precisely perceiving an indoor activity according to the present invention.

Referring to FIG. 3, in still another embodiment of the present invention, after step S12, the method may further include:

Step S14: Perform statistics of pace signals of the monitored person in a time period, analyze a change of the pace signals, and acquire body condition change information of the monitored person; and/or Step S15: Perform statistics of building vibration spectrum information, and analyze building change information according to a change of the vibration spectrum information.

By recognizing the pace signal of the monitored person, the slow change of the pace signal of the monitored person may be observed in a long term, and the health information of the monitored person may be acquired. In addition, the slow and long-term change information of the building may be acquired according to the change of the vibration spectrum of the building. In a specific embodiment of the present invention, for example, the numbness of the left foot of the monitored person before contracting a stroke makes the pace characteristic of the monitored person change obviously in a short time, and the bilateral balance changes to retarding of the left foot. The impact caused by the left foot walking on the floor is weakened, the left stride is reduced, the frequency of making paces by the left foot is reduced, and the discrepancy between the left foot and the right foot is obviously increased. Accordingly, the monitored person may be reminded. For another example, the vibration caused by closing a door seldom changes sharply. The spectrum of vibrating at ultra-low frequencies after the door is closed is related to the structure and temperature of the building. An initial normal vibration model may be created on the basis of long-term data summarization. If a slow long-term change occurs, the change of the ultra-low spectrum may quantitatively reflect the aging process of the building.

According to the method for precisely perceiving an indoor activity, the pace signal (impact strength, stride, cadence and/or bilateral symmetry and the like) of the monitored person may be used to reflect the mental and health conditions of a person; the change of the vibration, which is caused by the pace on the floor, may be used to reflect long-term slow changes of the building; and a relatively detailed record of the daily life and the daily habits of the monitored person may be kept by recording and observing the daily indoor activity location. All the foregoing tasks may be performed without disturbing the monitored person, and can resolve the concern about leakage of privacy of the monitored person, for example, the face, figure, and behavior of the monitored person.

Figure 4:
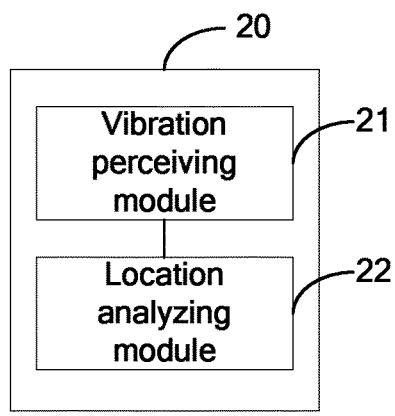
FIG. 4 is a schematic structural diagram in an embodiment of an apparatus for precisely perceiving an indoor activity according to the present invention.

Referring to FIG. 4, an embodiment of an apparatus 20 for precisely perceiving an indoor activity according to the present invention is provided. This apparatus 20 may include a vibration perceiving module 21 and a location analyzing module 22. The vibration perceiving module 21 is configured to receive a vibration signal on a floor by using multiple vibration sensors disposed according to a preset rule; and the location analyzing module 22 is configured to determine a location of a vibration source according to a phase difference of a vibration signal of the same vibration source in different vibration sensors.

According to the apparatus 20 for precisely perceiving the indoor activity, multiple vibration sensor that are at a relatively fixed distance between each other may sense the vibration caused by activities such as a walk on the floor, phase analysis may be performed on the vibration signals on the vibration sensors in different locations, the indoor movement of the vibration source (such as the monitored person) may be precisely located, and the information such as the activity status and the living habits of the monitored person is perceived.

The vibration source may be an indoor monitored human body, and the vibration signal may be a pace signal of the monitored person, and the pace signal may include an impact, a stride, a cadence, and/or bilateral symmetry or the like.

The vibration sensors disposed closely on the floor may sensitively perceive a slight vibration caused by the walk of a human being, the pass of an indoor truck, the fall of an object onto the ground, the locking of a door, and the like. The sensing of paces may be implemented by mathematical modeling. Although shoes and mental conditions impose a great influence on the impact caused by the walk, the stability of factors such as a basic house structure and a human weight makes the walk generate obviously distinguishable characteristics.

In this embodiment, there may be at least 3 vibration sensors, and a fixed distance is set between the vibration sensors; by performing phase shift analysis and sound speed calibration processing on the vibration signal in each vibration sensor, the location analyzing module 22 may perform a scan similar to B-ultrasound; and may acquire the accurate location of the vibration source by performing calculation with a trigonometric function according to the fixed distance between the vibration sensors. In a specific embodiment of the present invention, for example, signals received by 5 sensors that are arranged in a row and at a fixed distance between each other may be fit at different delays, scan and interception may be performed in a sector area that is almost 180° wide. Each distinguishing unit in a scan surface has a special and fixed delay characteristic for a different sensor. Therefore, by fitting the signals of different delays, the vibration scenario of the scan surface can be completely displayed. The distinguishing unit in which the vibration source is located takes on a high signal amplitude, and other units are silent. Like the reception in the phased array B-ultrasound scan, the present invention can clearly reflect the return wave conditions of the scanned vector surface in an image form, and therefore, can acquire the accurate location of the vibration source.

Figure 5:
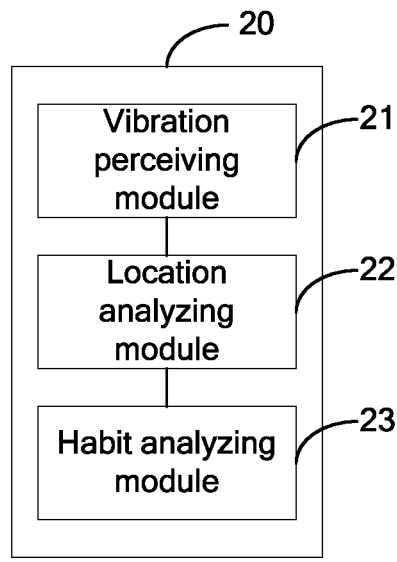
FIG. 5 is a schematic structural diagram in another embodiment of an apparatus for precisely perceiving an indoor activity according to the present invention.

Referring to FIG. 5, in another embodiment of the present invention, the apparatus 20 may further include: a habit analyzing module 23, configured to analyze living habits of the monitored person according to a location and the pace signal of the monitored person and time.

The multiple vibration sensors that are at a relatively fixed distance between each other are disposed closely on the floor, and may perceive the vibration on the floor and acquire the location of the vibration source. In recognizing the pace signal of the monitored person, tracking may be started. By analyzing the phase difference of the pace signal on different sensors, the current location of the monitored person who is walking can be precisely determined. The daily habit, the living status and the like of the monitored object can be acquired by means of combined analysis on the location information, the pace signal, and the time background.

Figure 6:
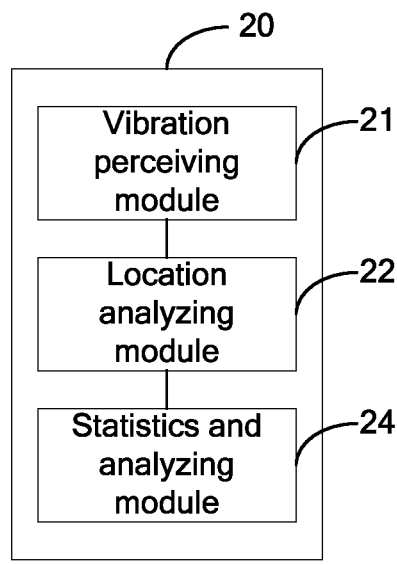
FIG. 6 is a schematic structural diagram in still another embodiment of an apparatus for precisely perceiving an indoor activity according to the present invention.

Referring to FIG. 6, in still another embodiment of the present invention, the apparatus 20 may further include: a statistics and analyzing module 24, configured to: perform statistics of pace signals of the monitored person in a time period, analyze a change of the pace signals, and acquire body condition change information of the monitored person; and perform statistics of building vibration spectrum information, and analyze building change information according to a change of the vibration spectrum information.

By recognizing the pace signal of the monitored person, the slow change of the pace signal of the monitored person may be observed in a long term, and the health information of the monitored person may be acquired. In addition, the slow and long-term change information of the building may be acquired according to the change of the vibration spectrum of the building. In a specific embodiment of the present invention, for example, the numbness of the left foot of the monitored person before contracting a stroke makes the pace characteristic of the monitored person change obviously in a short time, and the bilateral balance changes to retarding of the left foot. The impact caused by the left foot walking on the floor is weakened, the left stride is reduced, the frequency of making paces by the left foot is reduced, and the discrepancy between the left foot and the right foot is obviously increased. Accordingly, the monitored person may be reminded. For another example, the vibration caused by closing a door seldom changes sharply. The spectrum of vibrating at ultra-low frequencies after the door is closed is related to the structure and temperature of the building. An initial normal vibration model may be created on the basis of long-term data summarization. If a slow long-term change occurs, the change of the ultra-low spectrum may quantitatively reflect the aging process of the building.

According to the apparatus 20 for precisely perceiving an indoor activity, the pace signal (impact, stride, cadence and/or bilateral symmetry and the like) of the monitored person may be used to reflect the mental and health conditions of a person; the change of the vibration, which is caused by the pace on the floor, may be used to reflect long-term slow changes of the building; and a relatively detailed record of the daily life and the daily habits of the monitored person may be kept by recording and observing the daily indoor activity location. All the foregoing tasks may be performed without disturbing the monitored person, and can resolve the concern about leakage of privacy of the monitored person, for example, the face, figure, and behavior of the monitored person.

The foregoing descriptions are only exemplary embodiments of the present invention, and are not intended to limit the patent scope of the present invention. Any equivalent structure or equivalent process transformation made by using the specification of the present invention and content of the accompanying drawings, or used directly or indirectly in other related technical fields, shall also be covered in the patent protection scope of the present invention.

What is claimed is:

1. A method for precisely perceiving an indoor activity, comprising:
   receiving a vibration signal on a floor by using multiple vibration sensors disposed according to a preset rule; and
   determining a location of a vibration source according to a phase difference of a vibration signal of the same vibration source in different vibration sensors;
   wherein the vibration source is an indoor monitored human body, and the vibration signal is a pace signal of a monitored person, and the pace signal comprises an impact strength, a stride, a cadence, and/or bilateral symmetry;
   wherein the method further comprises:
   performing statistics of pace signals of the monitored person in a time period, analyzing a change of the pace signals, and acquiring body condition change information of the monitored person; and/or
   performing statistics of building vibration spectrum information, and analyzing building change information according to a change of the vibration spectrum information.

2. The method for precisely perceiving an indoor activity according to claim 1, wherein the step of determining a location of a vibration source according to a phase difference of a vibration signal of the same vibration source in different vibration sensors comprises:
   acquiring an accurate location of the vibration source by performing phase shift analysis and sound speed calibration processing on the vibration signal in each vibration sensor and by performing calculation with a trigonometric function according to a fixed distance between the vibration sensors, wherein at least 3 vibration sensors are disposed, and a fixed distance is set between the vibration sensors.

3. The method for precisely perceiving an indoor activity according to claim 1, wherein the method further comprises:
   analyzing living habits of the monitored person according to a location and the pace signal of the monitored person and time.

4. An apparatus for precisely perceiving an indoor activity, comprising:
   a vibration perceiving module, configured to receive a vibration signal on a floor by using multiple vibration sensors disposed according to a preset rule; and
   a location analyzing module, configured to determine a location of a vibration source according to a phase difference of a vibration signal of the same vibration source in different vibration sensors;
   wherein the vibration source is an indoor monitored human body, and the vibration signal is a pace signal of a monitored person, and the pace signal comprises an impact strength, a stride, a cadence, and/or bilateral symmetry;
   wherein the apparatus further comprises:
   a statistics and analyzing module, configured to: perform statistics of pace signals of the monitored person in a time period, analyze a change of the pace signals, and acquire body condition change information of the monitored person; and/or perform statistics of building vibration spectrum information, and analyze building change information according to a change of the vibration spectrum information.

5. The apparatus for precisely perceiving an indoor activity according to claim 4, wherein the location analyzing module is specifically configured to:
   acquire an accurate location of the vibration source by performing phase shift analysis and sound speed calibration processing on the vibration signal in each vibration sensor and by performing calculation with a trigonometric function according to a fixed distance between the vibration sensors, wherein at least 3 vibration sensors are disposed, and a fixed distance is set between the vibration sensors.

6. The apparatus for precisely perceiving an indoor activity according to claim 4, wherein the apparatus further comprises:
   a habit analyzing module, configured to analyze living habits of the monitored person according to a location and the pace signal of the monitored person and time.

* * * * *